US011954834B2

(12) United States Patent
Rauniyar et al.

(10) Patent No.: US 11,954,834 B2
(45) Date of Patent: Apr. 9, 2024

(54) SYSTEM AND METHOD FOR ENDOSCOPIC VIDEO ENHANCEMENT, QUANTITATION AND SURGICAL GUIDANCE

(71) Applicant: BOSTON SCIENTIFIC SCIMED, INC., Maple Grove, MN (US)

(72) Inventors: Niraj Prasad Rauniyar, Plymouth, MN (US); Robert J. Riker, Sewickley, PA (US); Timothy Paul Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/815,445

(22) Filed: Jul. 27, 2022

(65) Prior Publication Data

US 2022/0366553 A1 Nov. 17, 2022

Related U.S. Application Data

(63) Continuation of application No. 16/948,013, filed on Aug. 27, 2020, now Pat. No. 11,430,097.

(Continued)

(51) Int. Cl.
*G06T 7/246* (2017.01)
*A61B 1/00* (2006.01)
*A61B 5/06* (2006.01)
*G06T 3/00* (2006.01)
*G06T 3/4053* (2024.01)

(Continued)

(52) U.S. Cl.
CPC ............ *G06T 5/50* (2013.01); *A61B 1/00045* (2013.01); *A61B 5/065* (2013.01); *G06T 3/0012* (2013.01);

(Continued)

(58) Field of Classification Search
CPC ....... G06T 5/50; G06T 3/0012; G06T 3/0068; G06T 2207/10016; G06T 2207/10068;
(Continued)

(56) References Cited

U.S. PATENT DOCUMENTS

| 7,813,538 B2 | 10/2010 | Carroll et al. |
| 2004/0210105 A1 | 10/2004 | Hale et al. |

(Continued)

FOREIGN PATENT DOCUMENTS

| EP | 3142572 B1 | 10/2018 |
| JP | 2006065397 A | 3/2006 |

(Continued)

OTHER PUBLICATIONS

Rosa et al.,"An algorithm for calculi segmentation on ureteroscopic images", International Journal of Computer Assisted Radiology and Surgery, Mar. 2011, 11 pages.

(Continued)

*Primary Examiner* — Howard D Brown, Jr.
(74) *Attorney, Agent, or Firm* — Bookoff McAndrews, PLLC

(57) ABSTRACT

An endoscopic system includes an endoscopic imager configured to capture image frames of a target site within a living body and a processor configured to apply a spatial transform to a preliminary set of image frames, the spatial transform converting the image frames into cylindrical coordinates; calculate a map image from the spatially transformed image frames, each pixel position in the map image being defined with a vector of fixed dimension; align a current image frame with the map image and apply the spatial transform to the current image frame; fuse the spatially transformed current image frame to the map image to generate a fused image; and apply an inverse spatial transform to the fused image to generate an enhanced current image frame having a greater spatial resolution than the current image frame. The system also includes a display displaying the enhanced current image frame.

17 Claims, 11 Drawing Sheets

Related U.S. Application Data

(60) Provisional application No. 62/904,408, filed on Sep. 23, 2019.

(51) Int. Cl.
| | | |
|---|---|---|
| *G06T 5/50* | (2006.01) | |
| *G06T 7/32* | (2017.01) | |
| *G06T 7/55* | (2017.01) | |
| *G06T 7/70* | (2017.01) | |
| *H04N 23/50* | (2023.01) | |
| *G06K 9/32* | (2006.01) | |

(52) U.S. Cl.
CPC .......... *G06T 3/0068* (2013.01); *G06T 3/4053* (2013.01); *G06T 7/32* (2017.01); *G06T 7/55* (2017.01); *G06T 7/70* (2017.01); *H04N 23/50* (2023.01); *G06T 2207/10016* (2013.01); *G06T 2207/10068* (2013.01); *G06T 2207/20221* (2013.01); *G06T 2207/30084* (2013.01); *H04N 23/555* (2023.01)

(58) Field of Classification Search
CPC . G06T 2207/20221; G06T 2207/30084; G06T 3/0062; G06T 3/00; G06T 7/11; A61B 1/00045; A61B 5/065; A61B 17/00234; A61B 90/37; A61B 2017/00296; A61B 2090/372; A61B 2090/373; H04N 23/50; H04N 23/555

See application file for complete search history.

(56) References Cited

U.S. PATENT DOCUMENTS

| | | | | |
|---|---|---|---|---|
| 2005/0264813 | A1* | 12/2005 | Giakos | G01J 3/447 |
| | | | | 356/369 |
| 2008/0071143 | A1 | 3/2008 | Gattani et al. | |
| 2014/0276008 | A1* | 9/2014 | Steinbach | A61B 5/0059 |
| | | | | 600/424 |
| 2016/0361042 | A1* | 12/2016 | Razansky | A61B 8/0825 |
| 2017/0281102 | A1* | 10/2017 | Ken | G01N 37/005 |
| 2018/0174311 | A1* | 6/2018 | Kluckner | G06V 10/25 |
| 2019/0201109 | A1* | 7/2019 | Berlinger | G06T 7/248 |
| 2021/0090226 | A1* | 3/2021 | Rauniyar | G06T 3/0012 |

FOREIGN PATENT DOCUMENTS

| | | |
|---|---|---|
| JP | 2008289767 A | 12/2008 |
| JP | 2011139734 A | 7/2011 |
| JP | 2015146970 A | 8/2015 |
| JP | 2019150574 A | 9/2019 |
| TW | 201225001 A | 6/2012 |
| WO | 2017006708 A1 | 1/2017 |
| WO | 2019240257 A1 | 12/2019 |

OTHER PUBLICATIONS

Office Action in Japanese Application No. 2023-000266, dated Feb. 1, 2024 (2 pages).

* cited by examiner

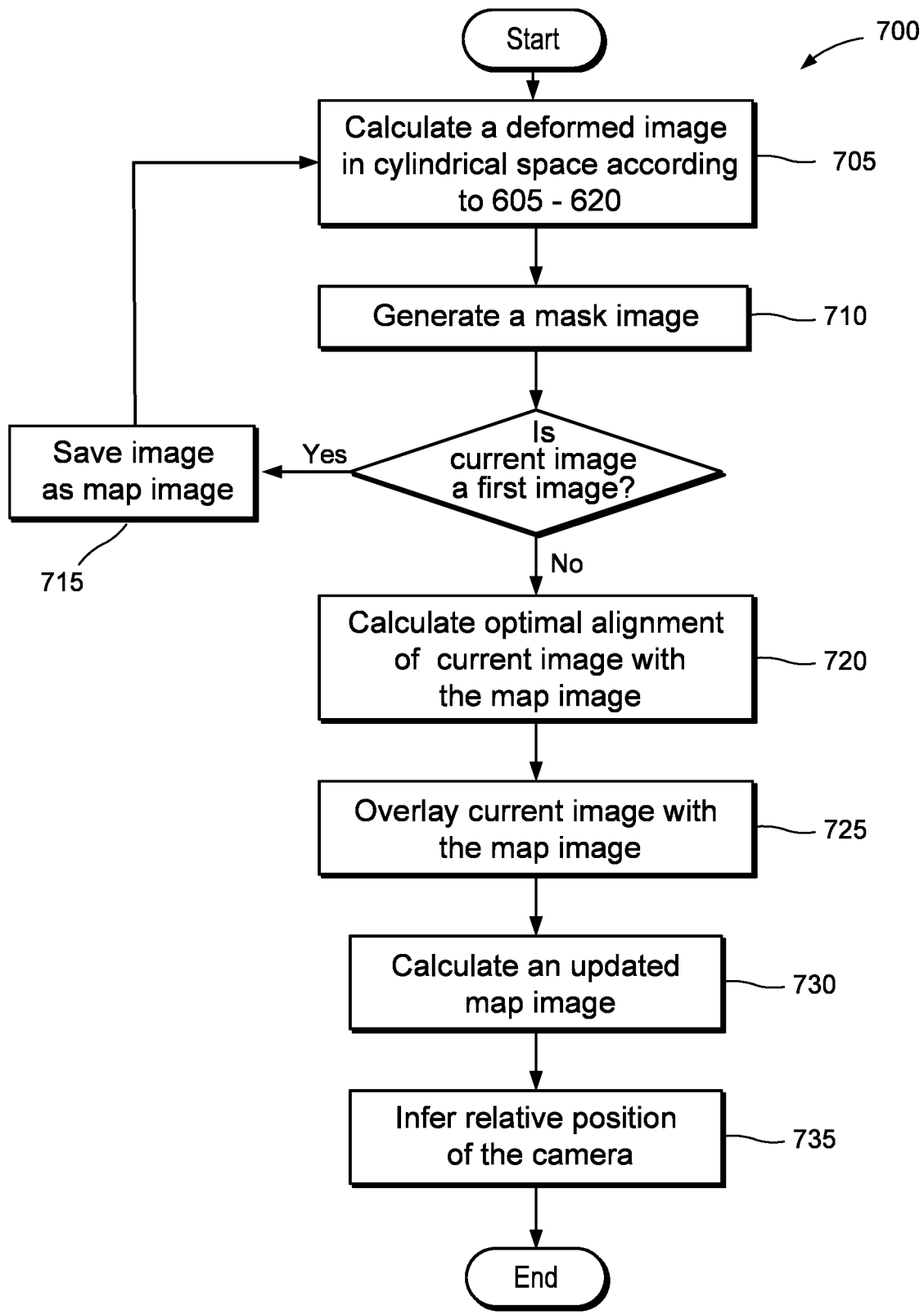
F I G. 10

SYSTEM AND METHOD FOR ENDOSCOPIC VIDEO ENHANCEMENT, QUANTITATION AND SURGICAL GUIDANCE

PRIORITY CLAIM

The present application is a Continuation of U.S. patent application Ser. No. 16/948,013 filed on Aug. 27, 2020, which claims priority to U.S. Provisional Patent Application Ser. No. 62/904,408 filed Sep. 23, 2019. The disclosures of the above application(s)/patent(s) are incorporated herewith by reference.

FIELD

The present disclosure relates to a system and a method for endoscopic video enhancement, quantitation and surgical guidance.

BACKGROUND

An endoscopic imager may be used during a variety of medical interventions. The view of the patient anatomy provided by the imager is limited by the resolution and the field of view of the scope. Such a limited view of the anatomy may prolong the intervention and fail to provide the operating physician with all of the information desired in performing the intervention.

SUMMARY

The present disclosure relates to an endoscopic system includes an endoscopic imager configured to capture image frames of a target site within a living body and a processor configured to apply a spatial transform to a preliminary set of image frames, the spatial transform converting the image frames into cylindrical coordinates; calculate a map image from the spatially transformed image frames, each pixel position in the map image being defined with a vector of fixed dimension; align a current image frame with the map image and apply the spatial transform to the current image frame; fuse the spatially transformed current image frame to the map image to generate a fused image; and apply an inverse spatial transform to the fused image to generate an enhanced current image frame having a greater spatial resolution than the current image frame. The system also includes a display displaying the enhanced current image frame.

In an embodiment, the spatial transform is generated based off an optical geometry of the endoscopic imager.

In an embodiment, the map image has a resolution that is an integer multiple greater than a resolution of the endoscopic imager.

In an embodiment, the current image frame is aligned with the map image based on a cross-correlation where a degree of similarity between the current image frame and the map image is measured.

In an embodiment, the processor is further configured to expand a field of view of the enhanced current image frame, as compared to the current image frame, based on an area of the map image surrounding the spatially transformed current image frame.

In an embodiment, the processor is further configured to add the spatially transformed current image frame to the map image.

In an embodiment, when a given pixel position in the map image is full, an oldest sample is deleted when a new sample is added.

The present disclosure also relates to an endoscopic system which includes an endoscopic imager configured to capture image frames of a target site within a living body and a processor. The processor is configured to: apply a spatial transform to a preliminary set of image frames, the spatial transform converting the image frames into cylindrical coordinates; calculate a map image from the spatially transformed image frames, each pixel position in the map image being defined with a vector of fixed dimension; calculate a scale space representation of the map image; capture further images comprising a plurality of independent regions; develop a non-linear spatial transform comprising independent spatial transforms for each of the independent regions when a predetermined amount of image data for each of the independent regions has been acquired; and derive a structure from motion (SFM) depth map from the non-linear spatial transform.

In an embodiment, the SFM depth map is further based on tracking information for the endoscopic imager, the tracking information comprising a changing pose of the endoscopic imager between captured images.

In an embodiment, the processor is further configured to: identify and segment scope-relative objects and interesting objects in the preliminary set of image frames; and exclude the identified scope-relative objects when the spatial transform is applied to the preliminary set of images.

In an embodiment, the processor is further configured to estimate a size for the interesting objects based on depth information and an angular extent in a current image frame.

In an embodiment, the endoscopic system further includes a display configured to display the current image frame with the interesting objects annotated.

In an embodiment, the interesting objects are kidney stones.

In an embodiment, the endoscopic system further includes an electromagnetic (EM) tracker attached to the endoscopic imager configured to provide tracking data comprising a six degree-of-freedom position for the endoscopic imager. The processor is further configured to segment a previously acquired 3D image volume of the target site. The tracking data is combined with the segmented image volume and the SFM depth map to provide a position estimate for the endoscopic imager.

In an embodiment, the processor is further configured to: deform the segmented image volume when the tracking data is shown to breach a surface of the segmented image volume.

In addition, the present invention relates to a method which includes applying a spatial transform to a preliminary set of image frames of a target site within a living body, the spatial transform converting the image frames into cylindrical coordinates; calculating a map image from the spatially transformed image frames, each pixel position in the map image being defined with a vector of fixed dimension; aligning a current image frame with the map image and applying the spatial transform to the current image frame; fusing the spatially transformed current image frame to the map image to generate a fused image; and applying an inverse spatial transform to the fused image to generate an enhanced current image frame having a greater spatial resolution than the current image frame.

In an embodiment, the spatial transform is generated based off an optical geometry of the endoscopic imager.

In an embodiment, the map image has a resolution that is an integer multiple greater than a resolution of the endoscopic imager.

In an embodiment, the current image frame is aligned with the map image based on a cross-correlation where a degree of similarity between the current image frame and the map image is measured.

In an embodiment, the method further includes expanding a field of view of the enhanced current image frame, as compared to the current image frame, based on an area of the map image surrounding the spatially transformed current image frame.

BRIEF DESCRIPTION

FIG. 10 shows a method for motion tracking in endoscopic video of a tubular structure according to a third exemplary embodiment.

DETAILED DESCRIPTION

Figure 1:
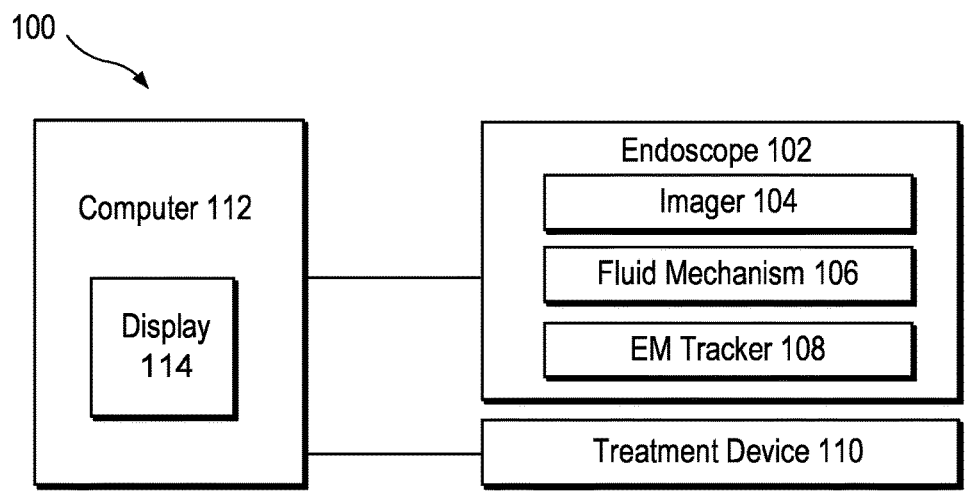
FIG. 1 shows a system for performing a urological procedure according to various exemplary embodiments of the present disclosure.

The present disclosure may be further understood with reference to the following description and the appended drawings, wherein like elements are referred to with the same reference numerals. The exemplary embodiments describe improvements to an endoscopic display for endoscopic procedures. The improvements include, e.g., enhancements of the endoscopic view and quantitative feedback on video object characteristics, particularly for urological procedures. Some common urological procedures include kidney stone management (e.g. lithotripsy), BPH (benign prostate hyperplasia) procedures (e.g. GreenLight™ laser surgery), prostatectomy, bladder tumor resection, uterine fibroids management, diagnostics, etc. Many of these procedures may be described as "see and treat."

A typical procedure has an imaging medium (e.g. LithoVue™ or any other endoscopic imager), a mechanism to provide fluid (for clearing field of view and/or distending the cavity) and a treatment mechanism (e.g. laser, RF energy). The exemplary embodiments may improve physician decision-making through quantitative feedback on video object characteristics, including physical size estimates, possible correlates of stone composition, differentiating various types of tissue, etc. The cognitive load and efficiency of the procedure may also be improved through surgical guidance with respect to, e.g., swipe speed, bubble size and density during a laser procedure, Randall's plaque determination during a renal examination, insertion point determination during water vapor therapy (e.g. Rezum™) or capsule depth during a BPH procedure.

In one exemplary embodiment a super-resolution technique is implemented to create a higher-resolution map image from a series of lower-resolution endoscopic images, e.g., ureteroscopic or cystoscopic images, and fuse a current image to the map image such that the combined image has the resolution of the map image. The exemplary techniques are particularly suited for urological procedures, however, certain embodiments may improve endoscopic viewing of other generally tubular patient anatomy (e.g. veins, esophagus, etc.) or non-tubular patient anatomy (e.g., the stomach) so long as the surrounding tissue is continuous and is disposed so that unique locations on the tissue may be mapped based on longitudinal and radial coordinates as described below. "Super-resolution" may generally be defined as an improved resolution image generated by fusing lower-resolution images.

In the present description the term "super-resolution" generally refers to the creation of image spaces for mapping an anatomy to improve a video display during an endoscopic intervention. A related embodiment describes the derivation of a Structure from Motion (SfM) depth map. Other exemplary techniques may improve a display in other ways. For example, a properly designed deep convolutional neural network (CNN) may be applied directly to pixel data to suppress noise in the images and/or highlight difference in tissue perfusion. The described techniques may be used alone or in combination, to be described in detail below.

FIG. 1 shows a system 100 for performing a urological procedure according to various exemplary embodiments of the present disclosure. The system 100 includes an endoscope 102 with an imager 104 for acquiring image frames of a patient anatomy during the urological procedure and a fluid mechanism 106 for providing a fluid (e.g., saline) to the anatomy to clear blood and debris that may impair the view of the imager 104. The endoscope 102 of this embodiment includes an optional electromagnetic (EM) tracker 108 to inform a determination of the position of the endoscope 102 relative to continuously deforming patient anatomy, as described in more detail below.

The system 100 may further include a treatment device 110, selected depending on the nature of the urological procedure. The treatment device 110 may be run through the endoscope 102 or may be external to the endoscope 102. For example, the treatment device 110 may be, e.g., a laser or a shockwave generator for breaking up kidney stones or a resectoscope for removing prostate tissue. When the urological procedure is for diagnostic purposes (i.e., for examining the anatomy and not for treating a condition), there may be no treatment device used. The exemplary embodiments are described with respect to urological imaging, however, the exemplary embodiments are not limited thereto. Certain embodiments may be applicable to (e.g., esophageal imaging), where a fluid mechanism is not used.

The system 100 includes a computer 112 processing image frames provided by the imager 104 and providing the processed images to a display 114. The computer 112 and the display 114 may be provided at an integrated station such as an endoscopic tower. Other features for performing the urological procedure may be implemented at the endoscopic tower, including, e.g., actuators controlling a flow rate for the fluid delivered through the fluid mechanism 106. The exemplary embodiments describe algorithmic processes for altering and enhancing the displayed images, generally on a continuous basis or in any other desired manner.

Figure 2:
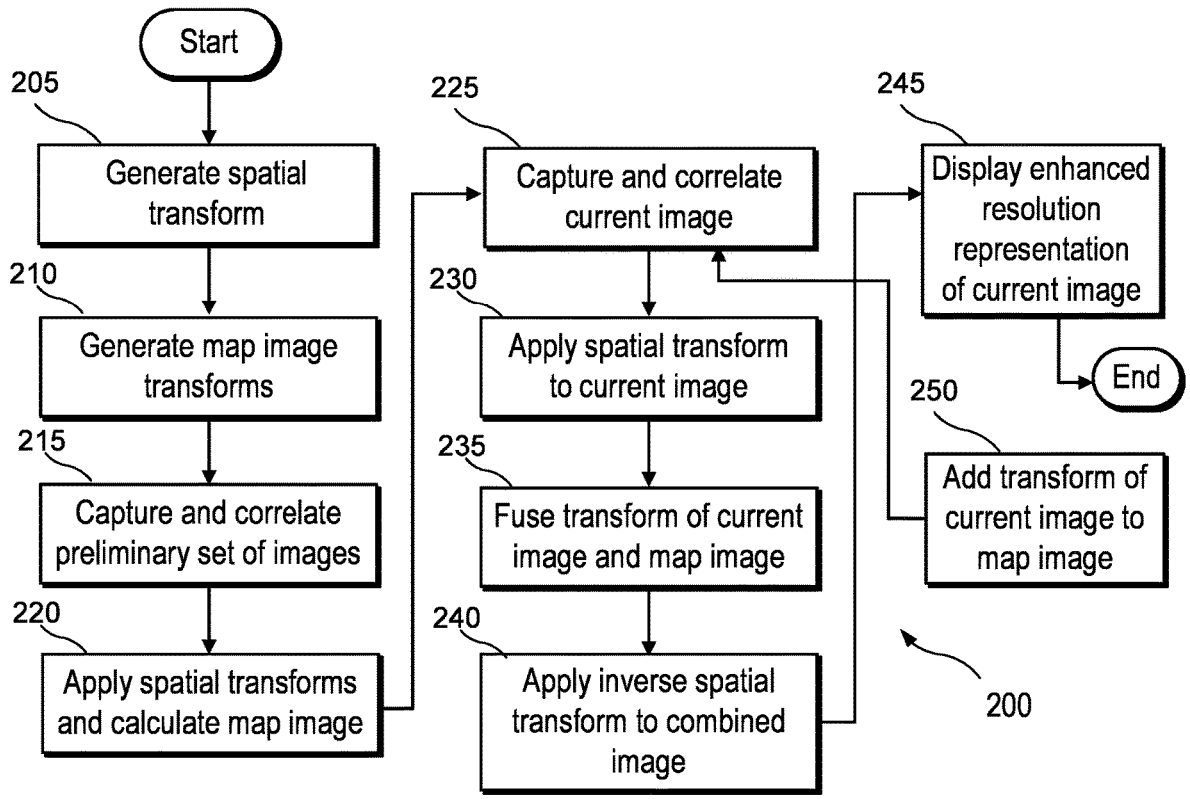
FIG. 2 shows a method for improving detail and/or a field view of an endoscopic video according to a first exemplary embodiment.
Figure 3:
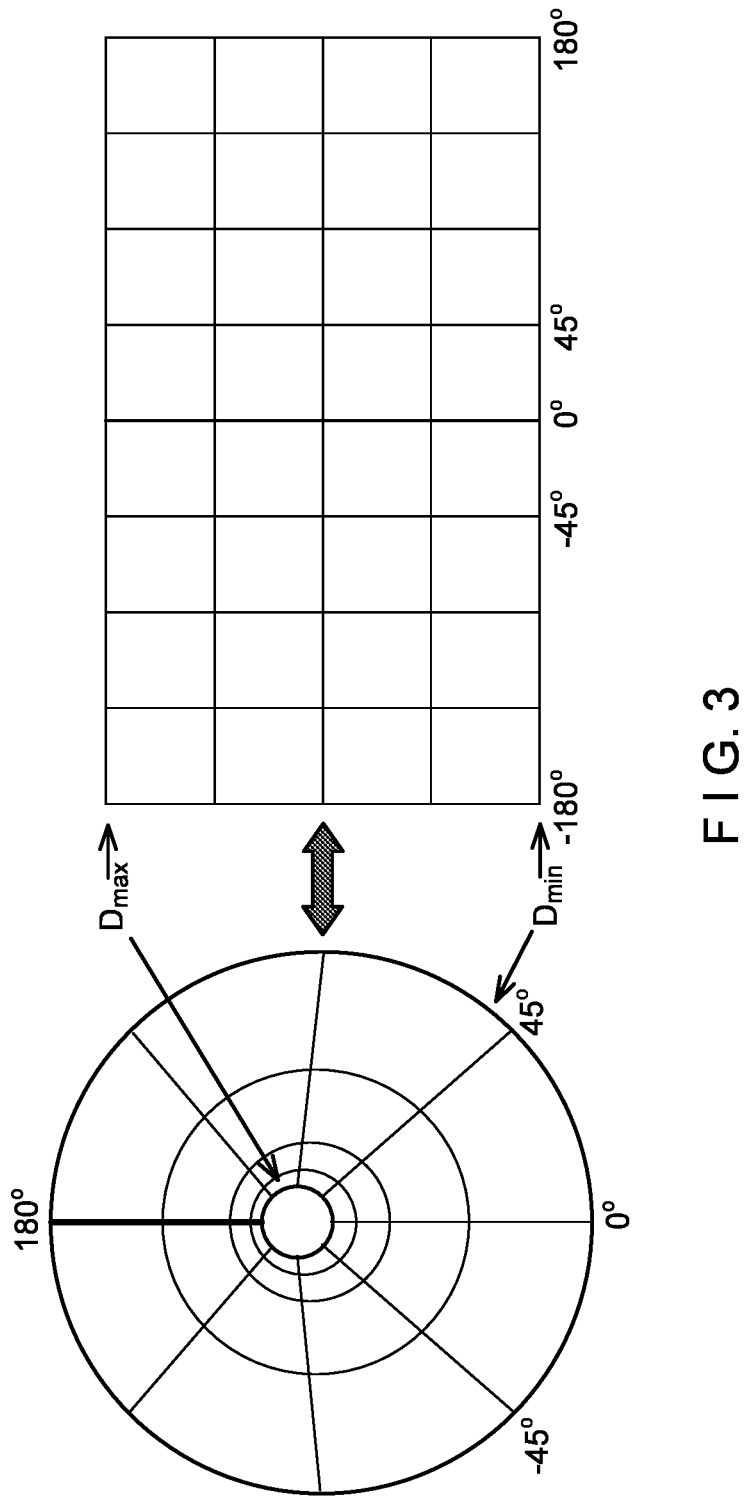
FIG. 3 shows a diagram of a spatial transform from image coordinates to cylindrical coordinates.

FIG. 2 shows a method 200 for improving detail and/or a field view of an endoscopic video display according to a first exemplary embodiment. The method 200 may be considered a super-resolution technique particularly suited for close-quarters endoscopic imaging of tubular structures, e.g., a urethra. In 205, a spatial transform is generated to convert an image from image coordinates into cylindrical coordinates, as shown in FIG. 3. The spatial transform is generated based off the optical geometry of the imager 104. An inner-most circle in FIG. 3 may or may not be mapped, with an expectation that at a small radius a number of data points available in the video display may be too few to be useful. As would be understood by those skilled in the art, the number of black circles on the left should correspond to the number of black horizontal lines on the right.

In 210, a set of transforms is generated for creating a map image in cylindrical space at a resolution that is an integer multiple of the resolution of the imager 104. For example, the map image may have a resolution, i.e., a number of pixels used to construct the map image, that is three times the resolution of the imager 104. Each of the pixel positions in the map is represented by a vector of fixed dimension. For example, the vector at a given position may have e.g. eight elements for representing eight samples accumulated from that position over multiple image frames.

In 215, a preliminary set of images captured by the imager 104 are correlated to align in the cylindrical coordinate system. In 220, the spatial transform is applied to the multiple image samples to convert the images into cylindrical coordinates, and a map image is calculated from the samples. The map image has each image position defined from the vector with an outlier rejection applied. For example, the outlier rejection may be a median filter.

In 225, a current image is captured by the imager and correlated to the map image to optimize the alignment of the images in the cylindrical space when the spatial transform is applied. For example, the correlation may be a cross-correlation between the images to measure a degree of similarity therebetween and align the images to maximize the similarities. In 230, the spatial transform is applied to the image based on the correlation. In 235, the current transformed image and the map image are combined, e.g. fused, in the cylindrical coordinate system. The field of view of the combined image may be expanded if the map image has sufficient data in the area surrounding the field of view of the current image.

In 240, an inverse spatial transform is applied to the combined image to generate an image with enhanced spatial resolution in the scope coordinate system. In 245, the enhanced resolution image is displayed on the display 114 to guide the endoscopic procedure with improved detail and/or an improved field of view as compared with the initially captured image at scope resolution.

In 250, the cylindrical coordinate transform of the image frame is added to the map image by adding the pixel values to the corresponding map vectors. The vectors may be ordered sequentially based on a time the sample was added such that, when the vector is full, the oldest sample is deleted and the new pixel values are added to the empty spot.

The image processing steps discussed above are performed on a continuous basis as new image frames are captured by the imager 104 although, as would be understood by those skilled in the art, other schedules for the image processing may be employed. Thus, each new image frame is visually enhanced with an improved resolution based on a fusion of the new frame with the map image.

Figure 4:
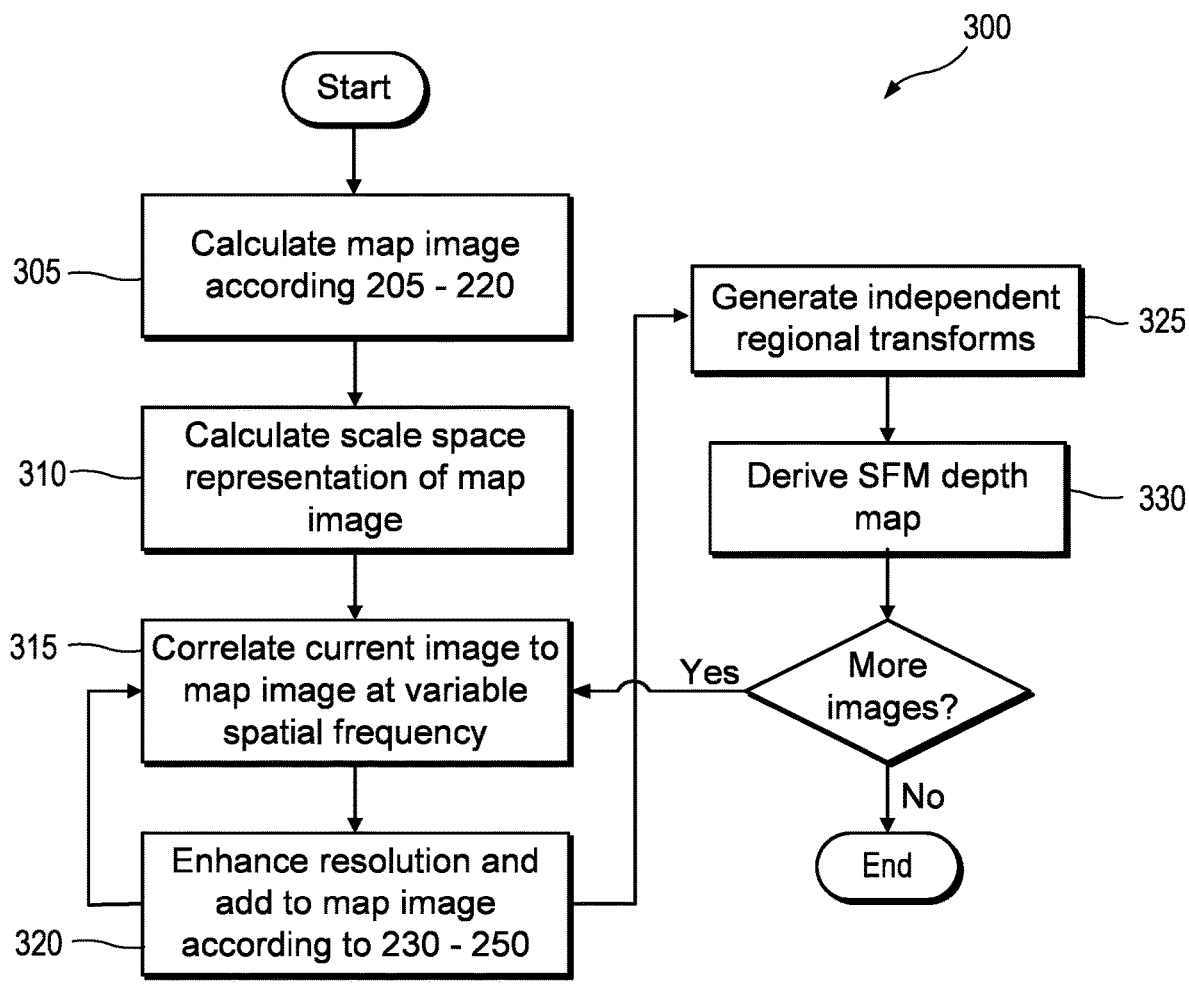
FIG. 4 shows a method for improving an endoscopic video according to a second exemplary embodiment.

FIG. 4 shows a method 300 for improving an endoscopic video according to a second exemplary embodiment. The method 300 is similar to the method 200, however the method 300 describes a non-rigid registration process to better compensate for optical distortions, tissue motion and point-of-view (POV) changes. Non-rigid registration generally refers to the application of a plurality of local transformations to an image to better correlate to a reference image (in this case the map image). In the present embodiment, different areas of the images may be transformed independently to better capture changes in position between the areas.

In 305, the map image is calculated according to steps 205-220 of the method 200. In 310, a scale space representation of the map image is calculated. A scale space representation generally refers to a representation of image data as a set of gradually smoothed images at different scales. For example, large-scale structures in the map image are emphasized while fine-scale structures are suppressed.

In 315, the current image is captured and correlated to the map image, initially at low spatial frequencies. In 320, the current image is fused with the map image and enhanced according to steps 230-250 of the method 200. The image processing steps are repeated as new images are acquired. However, as image data continues to be gathered to populate the map image, in 325, multiple independent regional transforms are developed by optimizing progressively smaller areas in progressively higher spatial frequency scales. Anatomy-relative motion may be estimated.

In 330, a Structure from Motion (SFM) depth map is derived based on the non-linear transform. SFM generally refers to a mapping of three-dimensional structures from a succession of images captured by a moving POV, where the changing position and orientation (pose) of the imager is tracked. The depth map is continuously populated as new images are gathered.

Elements of the aforementioned image processing methods 200, 300 may be used to further enhance displays in the following procedure-specific ways.

Kidney stone treatments, such as laser lithotripsy, may involve the fragmentation of a stone into many pieces of varying sizes, some of which would require further reduction, and some of which may be small enough to be retrieved or expelled naturally. Tracking stone particles in ureteroscopic video, inferring their size, and providing the physician with appropriate annotations may improve the speed, confidence and precision of these interventions. The following describes object sizing with respect to kidney stones, however, other image features may be sized and annotated in an endoscopic display such as, e.g., lesions, growths and other tissue features.

Figure 5:
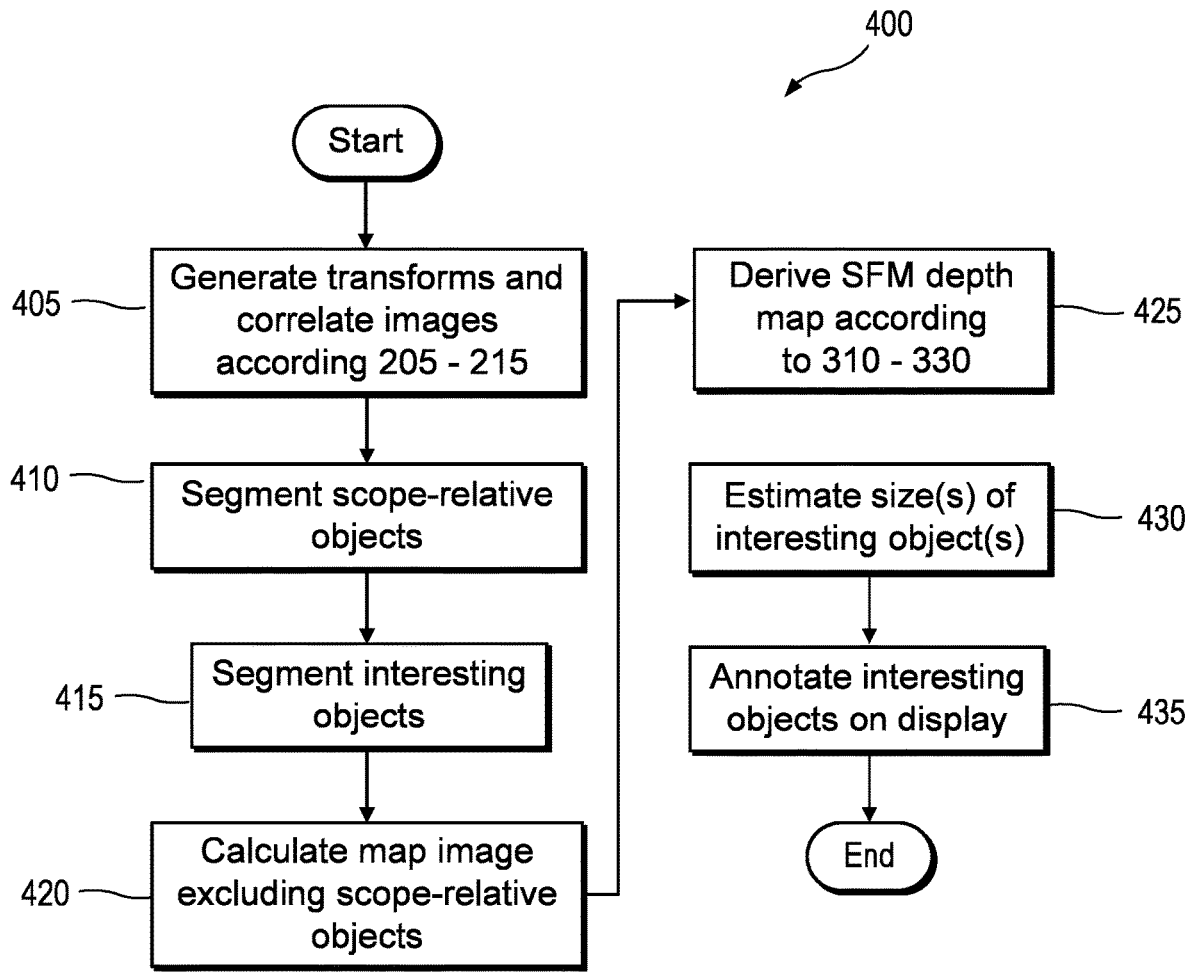
FIG. 5 shows a method for annotating an endoscopic video with object size information.

FIG. 5 shows a method 400 for annotating an endoscopic video with object size information. In 405, the spatial transform and image map are generated and the preliminary set of images is captured and correlated, according to steps 205-215 of method 200.

In 410, scope-relative objects are identified and segmented in the preliminary set of images. Scope-relative objects may include, e.g., a laser fiber for performing laser lithotripsy. The scope-relative object segmentation is implemented using predefined feature maps and constrained registration geometry.

In 415, interesting objects are identified and segmented in the preliminary set of images. Interesting objects may include, e.g., kidney stones. The interesting object segmentation is implemented using image features and blob-finding algorithms, as would be known by a person skilled in the art.

In 420, the spatial transform is applied to the preliminary set of images and the super-resolution scene map is calculated excluding the identified scope-relative objects.

In 425, a probabilistic depth map is derived according to steps 310-330 of method 300. The depth map is based off the independent regional transforms from the super-resolution map alignment and the implied camera pose transforms. The steps 310-330 include a continuous acquisition of images and a correlation/addition to the scene map to continuously improve the resolution of the scene map.

In 430, the sizes of the previously identified interesting objects are estimated based on depth information and angular extent in a currently captured image.

Figure 6:
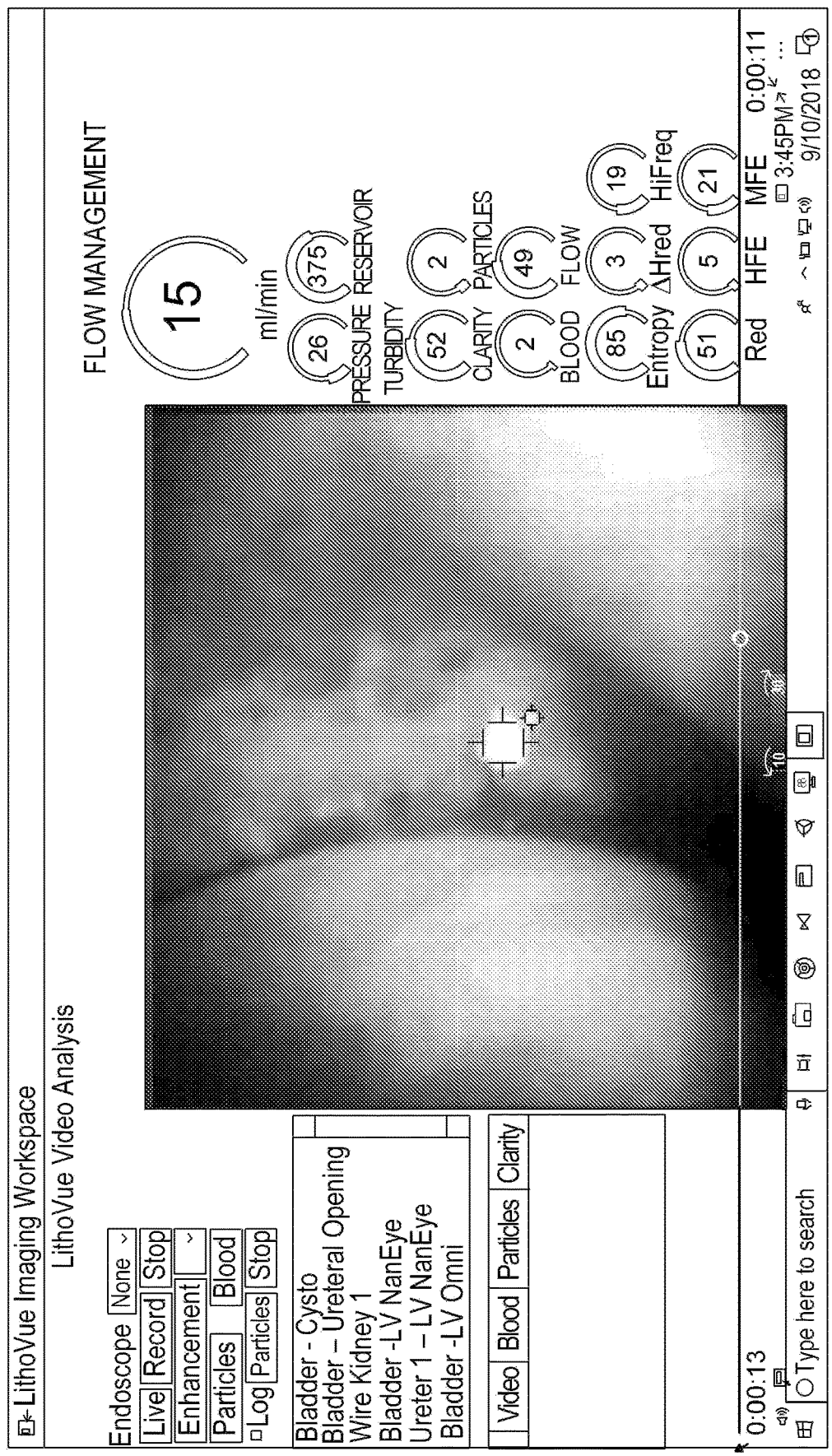
FIG. 6 shows an exemplary endoscopic video display where a kidney stone is bracketed.

In 435, the interesting objects, e.g., kidney stones, are annotated on the display of the currently captured image. In one embodiment, the dimensions of the object may be rendered directly on the display. In another embodiment, the objects may be annotated with brackets to show a boundary of the object. The brackets may be color-coded to show a size classification of the object by comparing the size estimate for the object with predefined treatment thresholds. For example, the brackets may be colored red when the size estimate indicates that the object requires further reduction, yellow when the size estimate indicates that the object is small enough for retrieval but too large for natural expulsion, and green when the size estimate indicates that the object may be passed naturally. In other words, the kidney stone may be annotated to indicate the smallest size of tube that the kidney stone can fit through. FIG. 6 shows an exemplary endoscopic video display where a kidney stone is bracketed.

In an alternate embodiment, the frame-to-frame correlation or super-resolution map described above is used to build a statistical description of color and albedo from multiple samples at each segmented pixel. Machine learning with clustering algorithms and in vivo training data is used to create a composition map for projecting probability of membership within identified size groups.

SFM techniques may be employed to inform a process for tracking an endoscope position during an endoscopic procedure. An SFM pose estimation for the endoscope, as determined from the endoscopic video, may be used in combination with position information from the EM tracker 108 and a segmented 3D reconstruction of the patient anatomy derived from previously acquired images to refine a position determination for the endoscope relative to a continuously deforming patient anatomy.

Figure 7:
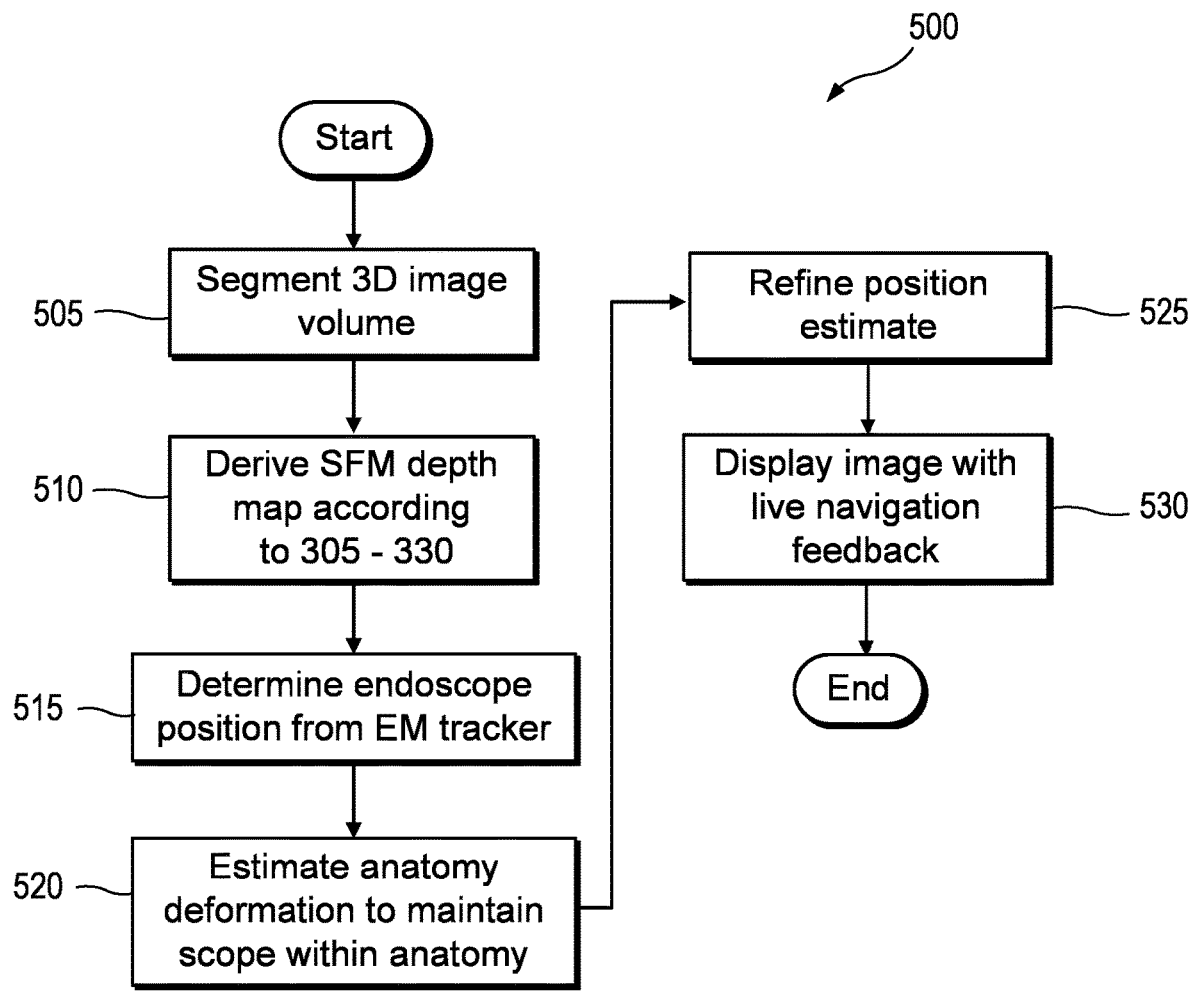
FIG. 7 shows a method for tracking an endoscope position relative to a continuously deforming anatomy according to a first exemplary embodiment.

FIG. 7 shows a method 500 for tracking the position of an endoscope relative to continuously deforming anatomy according to a first exemplary embodiment. In 505, a previously acquired 3D image volume of a target portion of anatomy is received and segmented. The 3D volume may be generated by previously captured CT images or images captured from a similar imaging medium. In 510, an SFM depth map is derived according to steps 305-330 of method 300. The depth map provides for anatomy-relative motion, a position estimate and a confidence level for the position estimates.

In 515, a six degree-of-freedom (6 DOF) position for the endoscope 102 is determined using the EM tracker 108 disposed near the tip of the endoscope 102. The 6 DOF position from 515 and the images populating the SFM depth map from 510 are received substantially simultaneously and may be correlated.

In 520, the position data from the EM tracker 108, the position data from the SFM map and the fixed volume of the anatomy are combined to estimate a minimal deformation of the anatomy sufficient to maintain the endoscope 102 within the surface boundaries of the anatomy. The resulting model assumes the scope 102 moves freely in the cavity until the position data indicates the scope 102 has contacted the segmented surface model. When the position data is shown to breach the surface of the fixed model, the anatomy is deformed to maintain the scope 102 position within the surface. For example, the anatomy displaces perpendicularly to the surface orientation.

In 525, the combined model and the 6 DOF endoscope position inform and improve the position estimation from the SFM depth map. The improved estimate prevents a runaway integration of noise.

In 530, the processed images are shown on the display 114 with live annotation navigation feedback. In an embodiment, the annotations may reflect positions of stones or particles from previous imaging. Additionally, by incorporating magnetic resonance (MR) tracking or optical tracking, the annotations may reflect paths that have already been navigated. The method is repeated continuously as images are acquired.

In an alternate embodiment, SFM techniques known in the art may be used rather than the SFM depth map derived in method 300. Compared to known techniques, the SFM depth map from method 300 has a simpler geometry, with less non-linearity necessary to represent typical transformations, e.g., those resulting from camera motion. Conventional SFM algorithms also require geometric corrections for camera optics, but these corrections do not extend to assumptions about surface continuity and orientation. If these assumptions are valid, they sharply reduce the numerical complexity of the solution, which in turn improves performance and reduces errors.

BPH (benign prostate hyperplasia) is a condition that may be treated through various minimally invasive transurethral endoscopic procedures. Knowledge of a position of the endoscope with respect to anatomical landmarks permits annotation of the endoscopic video, providing assistance to physicians in gauging distances and tracking an ongoing, multi-step intervention.

Figure 8:
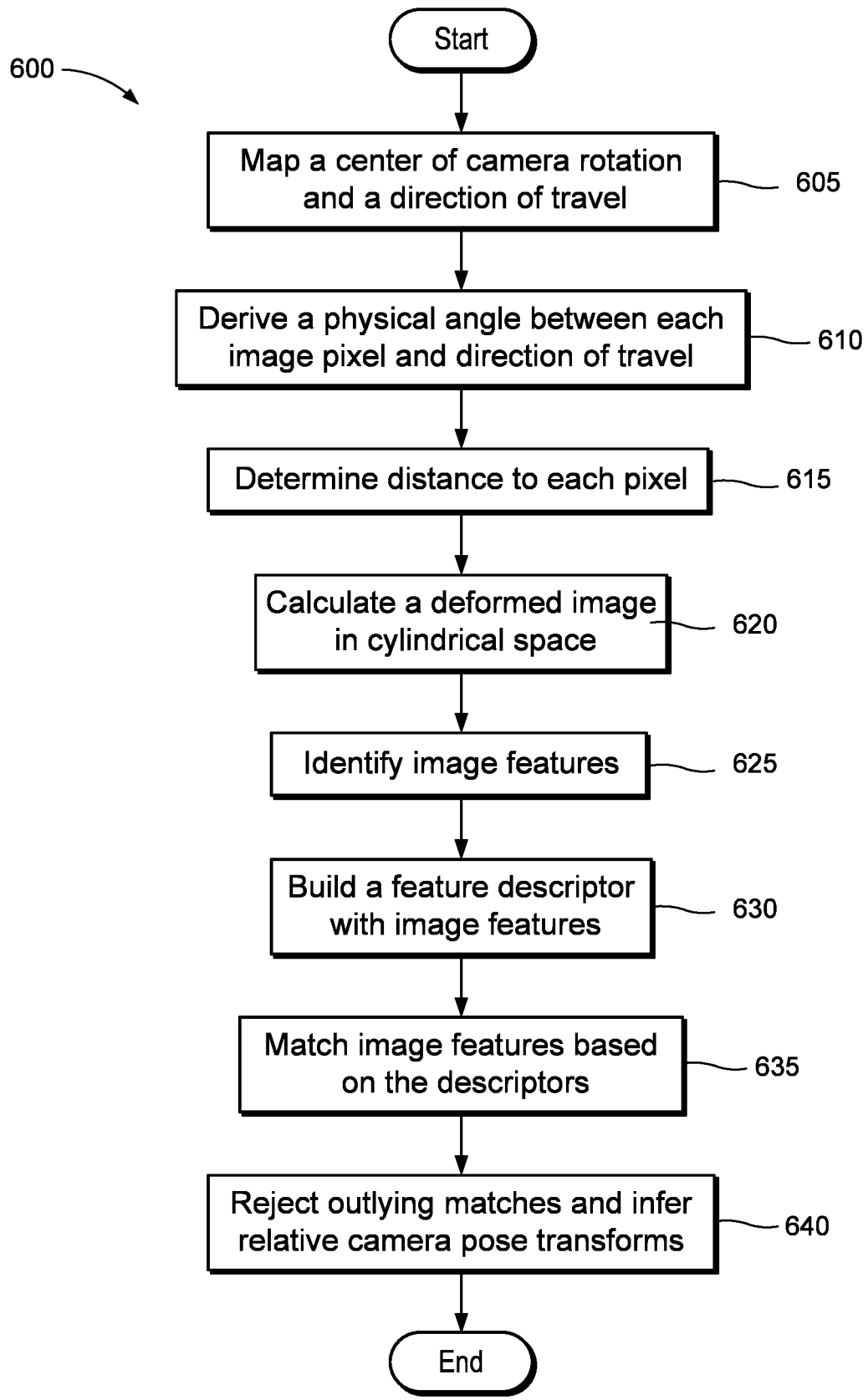
FIG. 8 shows a method for motion tracking in endoscopic video of a tubular structure according to a second exemplary embodiment.

FIG. 8 shows a method 600 for motion tracking in endoscopic video of a tubular structure, e.g., a urethra, according to a second exemplary embodiment. The method 600 may provide annotations including a current position relative to anatomical landmarks, desired positions associated with the intended intervention, and progress indicators relative to that intervention.

In 605, a center of camera rotation and a direction of travel are mapped. In 610, the optical system is mapped to derive a physical angle between each image pixel and the direction of scope travel, from the POV of the scope. Mapping the optical system effectively defines a scalar, as in a latitude, for each pixel of the image, that specifies angular distance from a camera axis (the North Pole, in the latitude analogy, except that 0° would be at the pole, and 90° at the equator, rather than vice versa). The "pole" position in the image, at 0°, is a point that remains directed at the same position when the camera is advanced or retracted exactly along the camera axis.

In 615, a distance to each anatomic pixel is determined for each image based on the mapping steps 605-610. The distance is measured from a reference plane perpendicular to the scope 102 to the object imaged at the pixel.

In 620, a deformed image is calculated in cylindrical space based on the determined distances and a rotation angle of the scope relative to its own axis. The deformed image is calculated relative to the vector from the point of scope rotation to a reference orientation feature in the scope video. An arbitrary feature is chosen to define the reference orientation (e. g., setting the 0° angle in FIG. 3), thus all subsequent mappings relate, directly or indirectly, to the reference orientation.

In 625, image features are identified. Saliency metrics such as, e.g. Hessian determinants, are calculated in scale space from the deformed cylindrical image to identify the image features.

In 630, a feature descriptor is built with image features related to any portion of interventional instruments within the field of view of the imager 104 being ignored. The feature descriptor is based on feature area pixel values in the cylindrical image. In 635, features are matched based on the descriptors. In an embodiment, present algorithms tend to match an image to another image, however, in another embodiment, a global map is possible and potentially advantageous. Unlike prior methods, it is not necessary to perform scale and rotation invariant calculations. By making inferences about the geometry of the scene map, the geometry of the features should remain in consistent scale and orientation from one image to the next. For example, the orientation of features is relative to the vector of the feature to a vanishing point of the extrapolated cylinder, such that if a nearby image is subsequently acquired with the scope rotated substantially along its axis, it will not affect this orientation angle, and the features can thereby be matched more directly.

In 640, outlying matches are rejected and relative camera pose transforms are inferred between image frames. Annotations would be expressed in terms of their relation to the reference feature and reference plane, and so once the camera pose transforms are known, the positions can be transformed back into image space.

Figure 9:
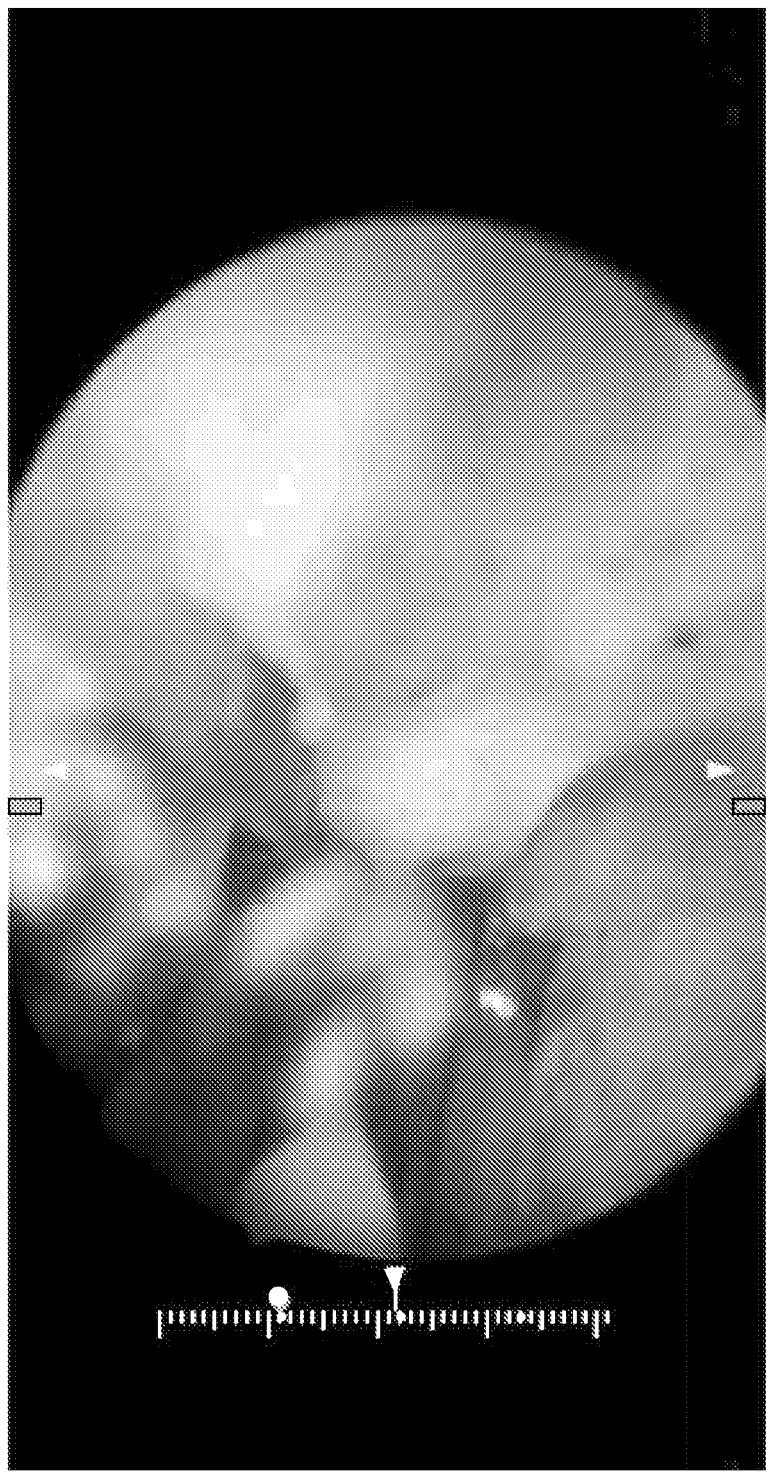
FIG. 9 shows an exemplary endoscopic video display with tracking annotations shown.

FIG. 9 shows an exemplary endoscopic video display where a current position relative to anatomic landmarks, a desired position associated with the intervention, and progress indicators relative to that intervention are shown.

FIG. 10 shows a method 700 for motion tracking in endoscopic video of a tubular structure according to a second exemplary embodiment. The method 700 is similar to the method 600. In 705, a deformed image is calculated in cylindrical space according to steps 605-620 of method 600.

In 710, a mask image is generated where pixels corresponding to instrument objects are ignored. If the current image is the first image, in 715, the mask image is saved as a map image.

If the current image is a subsequent image, in 720, an optimal alignment with the map image is calculated based on a suitable alignment criterion. For example, the optimal alignment may be calculated based on a correlation such as a Hessian-determinant weighted correlation or an entropy-weighted correlation. In 725, the image is overlaid with the map based on the optimal alignment.

In 730, an updated map image is calculated using a statistical combination of map position samples. For instance, the map image may be calculated using a median intensity of each color channel across all images where each pixel is defined. In 735, the relative position of the camera is inferred from the alignment with the map.

One procedure for treating BPH is laser prostatectomy, which shrinks or removes prostate tissue by passing a laser over the prostate tissue. The procedure is characterized by a sweep range (i.e., an angular range the laser passes over) and a sweep speed (i.e. an angle change per unit time) for the laser. The sweep range, sweep speed, and sweep angle are determined by a power density of the laser, a distance from the tissue to the laser, a type of tissue, a laser frequency, and a fiber size. Annotations may be incorporated to an endoscopic video feed to facilitate laser treatment procedures through increased physician awareness and precision.

Figure 11:
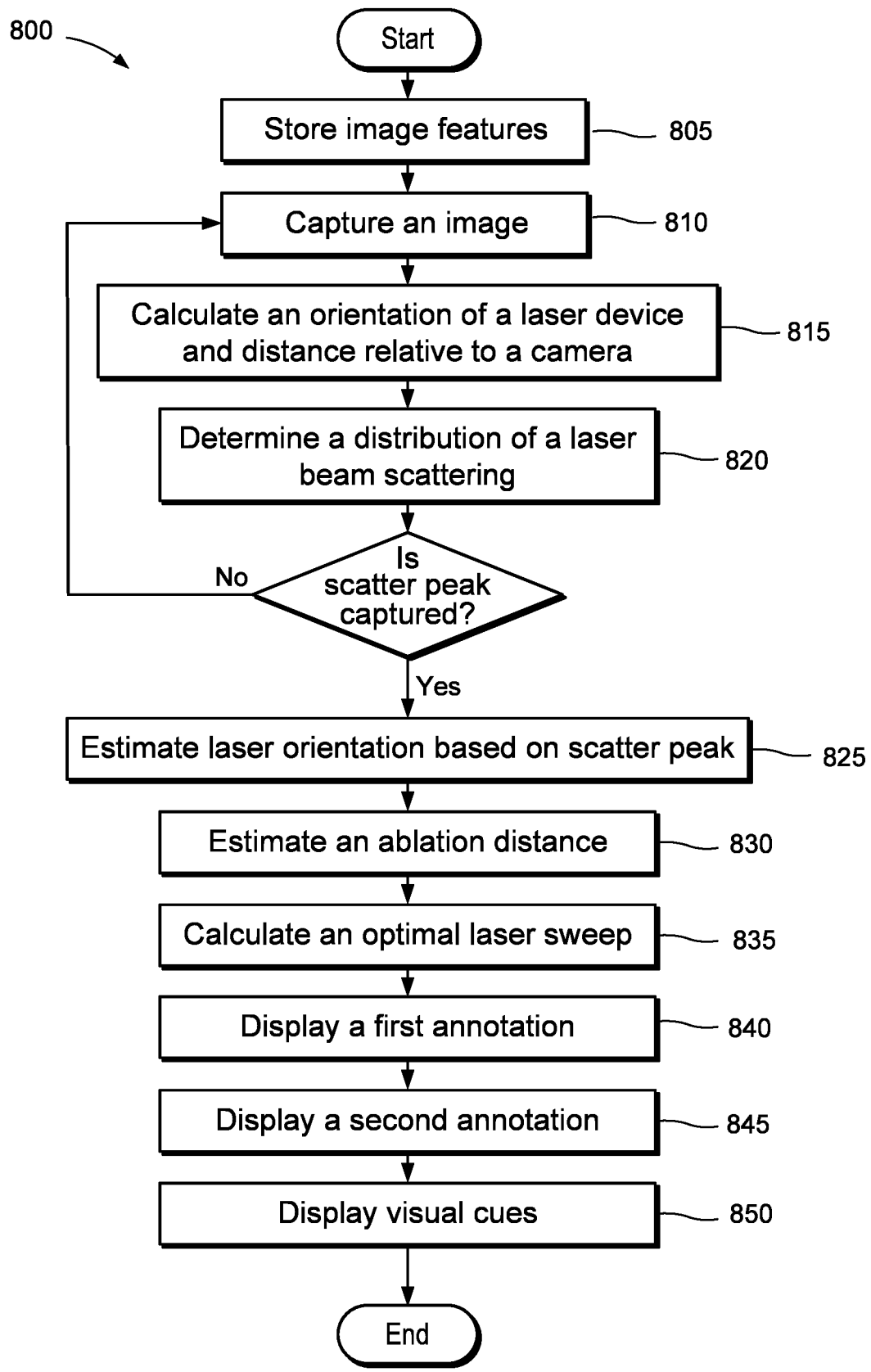
FIG. 11 shows a method for analyzing a cystoscopic video feed and providing annotations to inform a laser treatment procedure.

FIG. 11 shows a method 800 for analyzing a cystoscopic video feed and providing annotations to inform a laser treatment procedure, e.g., GreenLight™ laser. In 805, image features are stored for a laser device. In 810, an image is captured. In 815, an orientation of the laser device and a distance relative to the camera are calculated if the imager has captured at least a portion of the laser device in the image.

In 820, a distribution of a laser beam scattering is determined using color filtering. In 825, if a scatter peak is captured in the image, the laser orientation is estimated based on the scatter peak. The scatter peak is an intensity of reflected laser light, i.e. a bright spot that comes and goes with laser pulses, to infer a position in the anatomy directly in a path of the laser beam. Combined with direct visualization of an end of a laser fiber, an estimate of the laser orientation (as projected onto the camera sensor) is determined.

In 830, an ablation distance is estimated using a pre-calibrated map of a distance from the laser device to the scatter peak. The distance estimate may be refined using the distance calculation of step 815, if available.

In 835, an optimal laser sweep rate is calculated based on the distance estimate and a laser power setting. In 840, a first annotation is provided on the display 114 showing the optimal sweep rate and demonstrating a relation between the optimal sweep rate and a detected sweep rate.

In 845, a second annotation is provided on the display 114 showing an ablation depth. The displayed ablation depth may be relative to a distance to the capsule of the prostate.

In 850, visual cues are provided to illustrate a proper rate and a relationship between the optimal and measured rate and sweep angle.

Figure 12:
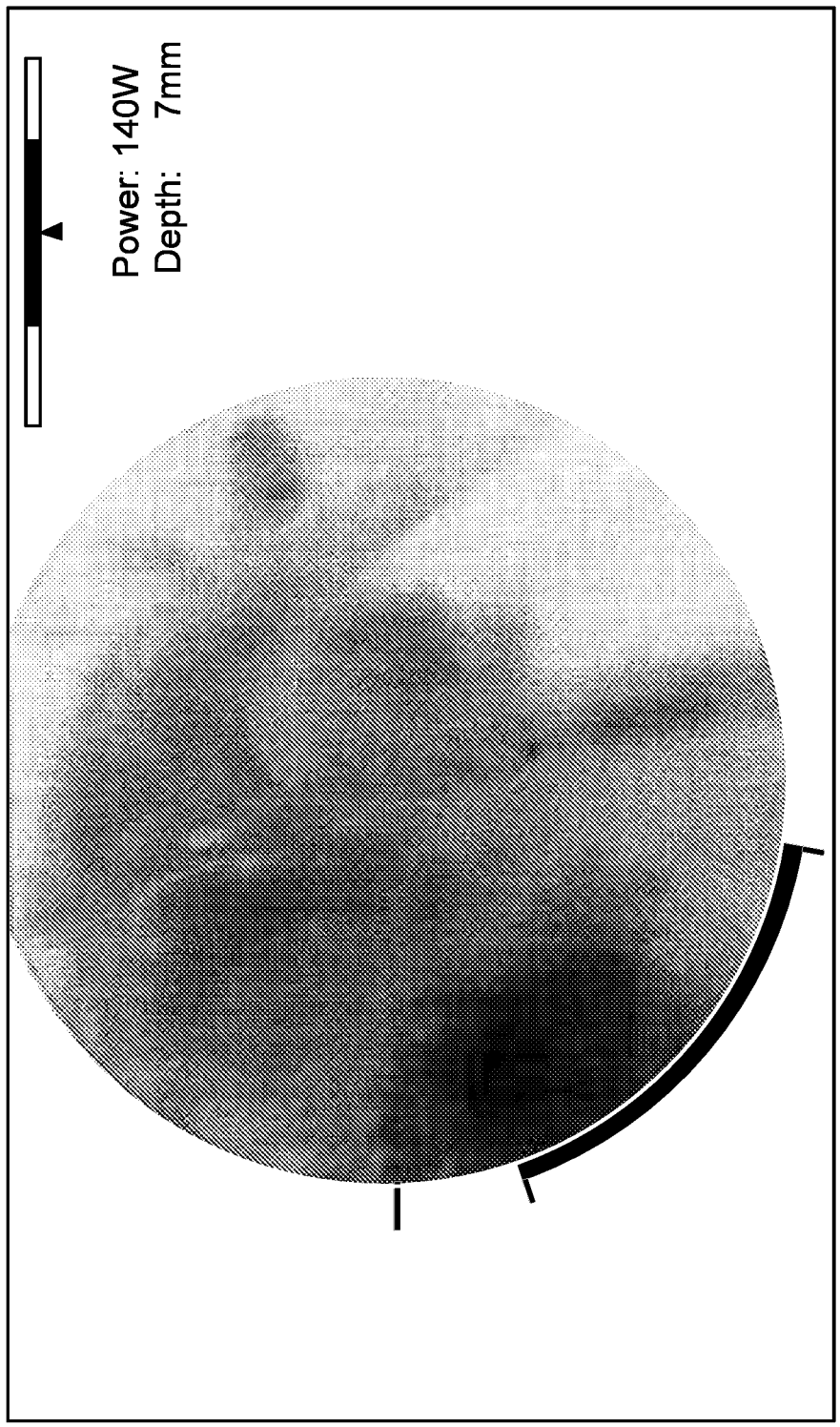
FIG. 12 shows an exemplary endoscopic video display with prostate laser annotations shown.

FIG. 12 shows an exemplary endoscopic video display with prostate laser annotations shown, including power level relative to an inferred optimal range, apparent average depth to laser-targeted tissue, inferred sweep angle, and optimal sweep angle/sweep pace calculated from power and average depth.

In an alternate embodiment, video annotations are provided comparing an apparent ablation depth at each sweep angle to a projected urethra-to-capsule distance measured in a previously acquired 3D image volume. Since the laser position is at a (former) urethral position, the distance to capsule measure in prior imaging provides a limit depth for the ablation procedure. A user may choose not to continue ablation at or beyond the capsule.

In still another alternate embodiment, angle and depth estimates are combined with laser angle and insertion depth measurements calculated from a 3D instrument tracking system.

Differentiating different types of tissue in an endoscopic view may further facilitate a variety of endoscopic procedures. An amplification of even very slight fluctuations in aligned image frames may allow for correlation to cardiac phase measurements and highlight differences in tissue perfusion.

In one embodiment, an appropriately designed convolutional neural network (CNN) may permit ad hoc tuning of filtering and amplification parameters to create a more flexible implementation than prior methods. The input volume of the CNN feeding the first convolutional layer would have a depth on the order of several seconds worth of video frames, times 3 for the red, green and blue color channels. The output layer would have the same length and width of the video frames, and a depth of 1, and represent the degree of cardiac correlation. The network would be trained on uncompressed in vivo endoscopic video with a cost function measuring the pixel's maximum time correlation to any of a series of predefined wavelets, scaled to match the specified cardiac interval. The resulting values, and maximum wavelet may drive amplification of the signals to derive differences in tissue perfusion and, relatedly, highlight differences in tissue makeup. Use of the CNN allows for the derivation in an unsupervised manner, whereas prior methods involve repeated user interventions to appropriately filter the raw image frames.

A CNN may also be employed to produce images with low noise and enhanced detail. A deep Convolutional Neural Network (CNN) may be applied directly to the pixel data from the endoscope. In this atypical CNN, the output volume has the same depth as the input volume (presumably 3, for the red, green & blue channels) but has a width & height that are the same integer multiple of the input width and height (the super-resolution multiplier), and fractional striding of convolution layers. The error term for training the network is calculated by performing discrete Hartley transforms on the original pixels, as well as the output values, and minimizing the squared difference, except where the highest spatial frequency component of the input data is shifted beyond its Nyquist limit to correspond with the highest spatial frequency representable in the output data transform. In an alternative embodiment, the spatial frequency transform of the input data is performed on a multi-frame average image computed using correlation-based registration transforms, to aid in noise suppression.

Various existing super-resolution or SFM methods may be combined with elements of the disclosed methods to improve the existing techniques. For example, the known/calibratable optical geometry of the endoscope, as discussed with respect to method 200, may be taken advantage of to improve existing super-resolution techniques. An image map generated based on the optical geometry of the endoscope may have 1 sample per pixel in each frame and the scope images may be transformed with known super-resolution techniques, such as "shift and fusion."

Other techniques for enhancing an image include applying various filters to the pixel data, such as band, median, or high frequency filters, and using edge detection for interesting objects through a cloudy or turbid environment. These further techniques may be used alone or in combination with the aforementioned embodiments.

The invention claimed is:

1. An endoscopic system, comprising:
  an endoscopic imager configured to capture image frames of a target site within a living body; and
  a processor configured to:
    map a center of imager rotation and a direction of travel of the imager;
    derive an angle between each pixel position and the direction of travel;
    determine a distance between each pixel position and the imager; and
    calculate a deformed image based on the determined distances and a rotation angle of the imager, the rotation angle being measured relative to an axis of the imager.

2. The endoscopic system of claim 1, wherein the processor is further configured to identify a plurality of image features.

3. The endoscopic system of claim 1, wherein the distance between each pixel position and the imager is measured from a reference plane perpendicular to the imager.

4. The endoscopic system of claim 1, wherein the deformed image is calculated in cylindrical coordinates.

5. The endoscopic system of claim 2, wherein the processor is further configured to:
  build a feature descriptor ignoring a first image feature identified as corresponding to a portion of an interventional instrument within a field of view of the imager; and
  match the image features based on the feature descriptors.

6. The endoscopic system of claim 5, wherein the processor matches the image features to the feature descriptors based on inferences about a geometry of the deformed image.

7. The endoscopic system of claim 5, wherein the feature descriptor is based on feature area pixel values in the deformed image.

8. The endoscopic system of claim 1, wherein the processor is further configured to:
  generate a mask image over pixels of the deformed image corresponding to interventional instruments within a field of view of the imager;
  capture a further image;
  calculate an optimal alignment of the further image with the mask image;
  overlay the further image with the mask image based on the optimal alignment;
  calculate an updated map image using a statistical combination of the further image and the mask image; and
  infer from the updated map a position of the imager corresponding to the further image relative to a position of the imager corresponding to the mask image.

9. An endoscopic system, comprising:
  an endoscopic imager configured to capture image frames of a target site within a living body;
  a laser device; and
  a processor configured to:
    store image features;
    calculate from a first one of the image frames an orientation of the laser device and a distance between the laser device and the imager;
    determine a distribution of a laser beam scattering; and
    determine whether a scatter peak was captured in the first one of the image frames.

10. The endoscopic system of claim 9, wherein the distribution of the laser beam scattering is determined using color filtering.

11. The endoscopic system of claim 9, wherein the processor is further configured to:
  estimate the orientation of the laser device based on the scatter peak;
  estimate an ablation distance from the laser device to the scatter peak using a pre-calibrated map; and
  calculate an optimal laser sweep rate based on the estimated ablation distance and a laser power setting.

12. The endoscopic system of claim 11, wherein the processor is further configured to:
   refine the estimated ablation distance using the distance calculated between the laser device and the imager.

13. The endoscopic system of claim 11, further comprising:
   a display configured to:
      display a first annotation showing the optimal sweep rate and a relation between the optimal sweep rate and a detected sweep rate; and
      display a second annotation showing an ablation depth.

14. The endoscopic system of claim 13, wherein the ablation depth is determined relative to a distance of a capsule to a prostate.

15. The endoscopic system of claim 11, further comprising:
   a display configured to display visual cues to illustrate the optimal sweep rate, a proper sweep rate, a detected sweep rate and a sweep angle of the laser device.

16. The endoscopic system of claim 9, wherein the processor is further configured to:
   calculate an angle of the laser device and insertion depth measurements using a 3D instrument tracking system.

17. An endoscopic system, comprising:
   an endoscopic imager configured to capture image frames of a target site within a living body;
   a processor configured to:
      apply a spatial transform to a preliminary set of image frames, the spatial transform converting the image frames into cylindrical coordinates;
      calculate a map image from the spatially transformed image frames, each pixel position in the map image being defined with a vector of fixed dimension;
      apply the spatial transform to a current image frame;
      fuse the spatially transformed current image frame to the map image to generate a fused image; and
      apply an inverse spatial transform to the fused image; and
   a display configured to display the enhanced current image frame.

* * * * *